(12) United States Patent
Varkuti

(10) Patent No.: US 12,011,290 B2
(45) Date of Patent: Jun. 18, 2024

(54) TIME-SYNCHRONIZED DEEP BRAIN STIMULATION OPTIMIZATION

(71) Applicant: Brainlab AG, Munich (DE)

(72) Inventor: Bálint Varkuti, Munich (DE)

(73) Assignee: BRAINLAB AG, Munich (DE)

( * ) Notice: Subject to any disclaimer, the term of this patent is extended or adjusted under 35 U.S.C. 154(b) by 340 days.

(21) Appl. No.: 16/336,001

(22) PCT Filed: Nov. 8, 2017

(86) PCT No.: PCT/EP2017/078607
§ 371 (c)(1),
(2) Date: Mar. 22, 2019

(87) PCT Pub. No.: WO2018/091331
PCT Pub. Date: May 24, 2018

(65) Prior Publication Data
US 2020/0022650 A1     Jan. 23, 2020

Related U.S. Application Data

(63) Continuation-in-part of application No. PCT/EP2016/078037, filed on Nov. 17, 2016.

(51) Int. Cl.
*A61B 5/00*          (2006.01)
*A61B 5/053*        (2021.01)
(Continued)

(52) U.S. Cl.
CPC .......... *A61B 5/4893* (2013.01); *A61B 5/0042* (2013.01); *A61B 5/0536* (2013.01); *A61B 5/055* (2013.01); *G01R 33/4806* (2013.01)

(58) Field of Classification Search
USPC ....................................................... 600/411
See application file for complete search history.

(56) References Cited

U.S. PATENT DOCUMENTS

2005/0010261 A1    1/2005   Luders et al.
2006/0017749 A1    1/2006   McIntyre et al.
(Continued)

FOREIGN PATENT DOCUMENTS

JP          2014513224 A    6/2014
WO    WO2012054612 A1    4/2012
(Continued)

OTHER PUBLICATIONS

International Search Report and Written Opinion of PCT Application PCT/EP2017/078607, dated Jan. 18, 2018.

*Primary Examiner* — Jason M Ip
*Assistant Examiner* — Renee C Langhals
(74) *Attorney, Agent, or Firm* — Gray Ice Higdon

(57) ABSTRACT

A medical data processing method is provided and includes: acquiring medical image data describing a digital image of an anatomical body part containing at least one nerve fibre extending between an internal part of the anatomical body part and a substantially exterior part of the anatomical body part; and acquiring atlas data describing an image-based model of the anatomical body part. The method determines, based on the medical image data and the atlas data, exterior part data describing an association between the exterior part and the nerve fibre. The method further acquires a predetermined applied stimulation signal applied to, based on the exterior part data, the exterior part and an emitted stimulation signal emitted by the nerve fibre. Correspondence measure data describing a measure of correspondence between the applied stimulation signal and the emitted stimulation signal is then determined.

20 Claims, 5 Drawing Sheets

(51) Int. Cl.
    *A61B 5/0536*    (2021.01)
    *A61B 5/055*     (2006.01)
    *G01R 33/48*     (2006.01)

(56) References Cited

U.S. PATENT DOCUMENTS

| | | | |
|---|---|---|---|
| 2009/0118635 A1 | 5/2009 | Lujan et al. | |
| 2011/0264165 A1* | 10/2011 | Molnar | A61N 1/36185 |
| | | | 607/45 |
| 2011/0295350 A1* | 12/2011 | Mercanzini | A61B 5/24 |
| | | | 607/116 |
| 2013/0178693 A1* | 7/2013 | Neuvonen | A61B 5/0042 |
| | | | 600/13 |
| 2013/0268019 A1* | 10/2013 | Gupta | A61N 1/36164 |
| | | | 607/45 |
| 2014/0039577 A1 | 2/2014 | Kothandaraman et al. | |
| 2015/0164366 A1* | 6/2015 | Lachner | G16H 20/00 |
| | | | 600/410 |
| 2016/0015994 A1* | 1/2016 | Cabrerizo | A61B 5/486 |
| | | | 600/14 |

FOREIGN PATENT DOCUMENTS

| | | | | |
|---|---|---|---|---|
| WO | WO-2013011474 A2 * | 1/2013 | | A61N 1/0553 |
| WO | WO-2015138981 A1 * | 9/2015 | | A61B 5/4035 |
| WO | WO2018091331 A1 | 5/2018 | | |

\* cited by examiner

TIME-SYNCHRONIZED DEEP BRAIN STIMULATION OPTIMIZATION

The present invention relates to a computer-implemented method for determining a stimulated nerve fibre disposed in an anatomical body part of a patient's body, a corresponding computer program, a non-transitory program storage medium storing such a program and a computer for executing the program, as well as a system for determining a stimulated nerve fibre disposed in an anatomical body part of a patient's body.

TECHNICAL BACKGROUND

After implanting deep brain stimulation (DBS) electrodes, programming of the stimulation settings is done on the basis of test stimulations and the in turn observed behaviour (e.g. the monopolar review) or (complementary) on the basis of anatomical programming (localizing the electrode in the patient's brain and assuming which is the intended target structure to be stimulated, then in turn modification of the stimulation parameters in order to reach optimal coverage of the target structure). However in some cases it is unclear for directional brain stimulation systems which way certain electrode contacts are actually pointing after implantation and therefore anatomical programming can become challenging. Furthermore in some cases the behavior is either not immediately observable (dystonia) because the effects only occur after chronic stimulation on a longer timescale or the behavior is not of an immediately observable nature (such as in the case of DBS for psychiatric disorders).

There are examples of brain stimulation devices such as deep brain stimulation electrodes being tuned to stimulate an area around the electrode which in recordings shows a specific activity, such as a high power in the beta band in the case of DBS for Parkinson's disease. However, that is the recording of a passive phenomenon, rather than capturing a tonic or phasic stimulation effect initiated by a second implanted or non-invasive device.

Previous solutions could not be applied for the treatment of psychiatric disorders or other disorders without immediate behavioral effect or clear neurophysiological marker.

Furthermore, there exists a problem in that it is difficult to judge whether a certain nerve fibre in the brain associated with a specific functional region (such as the speech region) of the brain has been stimulated by the DBS electrode as desired, when the electrode is tested during implantation. The reason is that, due to the circumstances of surgery, the patient may be narcotized and therefore unconscious so that he cannot co-operate with the medical team to give a neurological response when the stimulation by the electrode is activated The present invention is designed to provide a method and system for determining whether a stimulation signal has stimulated a desired nerve fibre and/or functional region in an anatomical body part such as the brain.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method encompasses reading data describing an applied electromagnetic neurological stimulation signal applied by external irradiation to a cortex region which is connected to a predetermined nerve fibre. In response to the stimulation signal neural impulses are transmitted through the nerve fibre. Corresponding measurement data describing the emitted stimulation signal is read by the disclosed method. The emitted stimulation signal can be compared to the applied stimulation signal to determine whether a measurement device (such as an electrode also suitable for deep brain stimulation) has been placed correctly relative to the nerve fibre. The comparison can include reading data describing a physical reaction of the tissue surrounding the measurement device, such as change in impedance or a change in the power spectrum of the electric field potential surrounding the measurement device.

GENERAL DESCRIPTION OF THE PRESENT INVENTION

In this section, a description of the general features of the present invention is given for example by referring to possible embodiments of the invention.

In general, the invention reaches the aforementioned object by providing, in a first aspect, a computer-implemented medical method for determining a stimulated nerve fibre disposed in an anatomical body part of a patient's body. The method is for example a data processing method and comprises executing, on at least one processor of at least one computer (for example at least one computer being part of a deep brain stimulation calibration or tuning system), the following exemplary steps which are executed by the at least one processor.

In a (for example first) exemplary step, medical image data is acquired which describes (for example defines or represents) a digital image of the anatomical body part is acquired. The medical image data has been generated by imaging the anatomical body part which belongs to the patient's body by applying a medical imaging modality to the anatomical body part. The medical image data may therefore be called patient image data. The medical image data may have been generated before execution of the disclosed method starts, but in one example of the disclosed method, generation of the medical image data is performed as a step of the disclosed method.

The imaging modality used for generating the medical image data is for example a tomographic imaging modality such as at least one of a computed x-ray tomography (CT), a magnetic resonance tomography (MR), a positron emission tomography (PET) or an ultrasound tomography (sonography). In a specific example, the imaging modality is diffusion-weighted magnetic resonance imaging (MRI) (generated for example by magnetic resonance diffusion tensor imaging—MR-DTI).

Generally, the anatomical body part may be any anatomical body part containing at least one nerve fibre which may be electromagnetically stimulated from the outside of the anatomical body part and for example runs close to the surface of the anatomical body part, but of course still within the anatomical body part. In a more specific example, the anatomical body part is the brain and the exterior part is the cortex (brain cortex). The anatomical body part contains at least one nerve fibre extending in a direction between an internal part of the anatomical body part and a substantially exterior part of the anatomical body part. The substantially exterior part is a region of the anatomical body part which lies close to the external surface of the anatomical body part and in a more specific example encompasses the external surface. The external surface need not be an external surface of the patient's body (such as the epidermis) but in a general case is a surface of the anatomical body part which limits the extent of the anatomical body part in a direction towards the external surface of the patient's body. Specifically, the exterior part lies closer to the external surface than other regions of the anatomical body part, specifically a region in which a deep brain stimulation electrode has been placed. Notably, placement of such an electrode is not part of the disclosed method. Furthermore, execution of the disclosed method does not require the electrode to be placed while the disclosed method is executed.

In a further (for example second) exemplary step, atlas data is acquired which describes (for example defines or represents) an image-based model of the anatomical body part including a representation of the at least one nerve fibre. The atlas data has generally been generated using at least the same imaging modality as the one used for generating the medical image data. In one example, the image-based model also includes a representation of the exterior part.

The atlas data may describe a multimodal atlas of the anatomical body part in which models of the anatomical body parts are stored which have been generated with each a different imaging modality, and a transformation rule between anatomically corresponding parts of the models. That allows for a transformation of the medical image data into an imaging modality which is different from the one which was used for its generation, for example to make the medical image data comparable to that different imaging modality. The transformation rule may be based on tissue class information stored for each model which describes the image appearance (e.g. colour value such as a multi-colour value or a greyscale value) of the constituents of the anatomical body part in the respective imaging modality.

Furthermore, the atlas data may have been generated from medical images of the anatomical body part of a plurality of patients. Alternatively, the atlas data may have been generated from at least one medical image of the anatomical body part of only the specific patient for whom the medical image data was generated, i.e. the model may be part of a patient-specific atlas.

The atlas data comprises for example positional information defined in a three-dimensional coordinate system. For example, the atlas data has been generated from tomographic images of the anatomical body part. In one example, the atlas data contains positional information describing (for example, defining or representing) a relative position between the exterior part and the nerve fibre in the image-based model. For example, the atlas data contains information describing (for example, defining or representing) the position of each of the exterior part and the nerve fibre in the positional reference system (e.g. coordinate system) used for defining positions in the image-based model. From that information, the relative position between the position of the exterior part and the position of the nerve fibre can be calculated. The information about the position of each of the exterior part and the nerve fibre therefore also defines the relative position.

In a further (for example third) exemplary step, exterior part data is determined which describes (for example, defines or represents) an association between the exterior part and the nerve fibre. In one example, the exterior part data describes a position of the exterior part in the anatomical body part (in at least one of the reference system used to define positions in the atlas data or the reference system used to define positions in the medical image data). Specifically, the exterior part data comprises information indicating that the nerve fibre runs into and/or through the exterior part. The exterior part data is determined based on the medical image data and the atlas data. For example, the exterior part data may be included in the atlas data. For example, the exterior part data may be determined by establishing a transformation (such as a positional mapping which may be represented by a matrix multiplication) between the atlas data and the medical image data. To this end, for example an image fusion algorithm may be executed for fusing the atlas data and the medical image data. The output of the image fusion algorithm will be a rule for mapping the medical image data onto the atlas data and/or the atlas data onto the medical image data so that corresponding anatomical structures are mapped at least substantially onto one another. Thereby, the position of a specific nerve fibre present and/or selected (for example, manually or automatically by image segmentation) from the medical image data (specifically, from the digital image) can thereby determined in the image-based model. In the model it is known which exterior part such as cortex region is connected to that nerve fibre (for example, it is known through or into which exterior part such as cortex region the nerve fibre runs). This allows to generate the exterior part data which includes information about the exterior part (such as its name or position) in at least the image based model. By knowledge of the positional mapping between the medical image data and the atlas data, the corresponding exterior part can be determined in the medical image data (in the digital image) and/or on the patient's body itself. In one example, the association between the exterior part and the nerve fibre comprises at least one of a relative position between the exterior part and the nerve fibre or a nerve stimulus-propagating connection between the exterior part and the nerve fibre.

In a further (for example fourth) exemplary step, stimulation signal data is acquired which describes (for example, defines or represents) a predetermined (i.e. at least one of known or fixed) applied stimulation signal applied to the exterior part. Knowledge of the position of the exterior part is advantageous for application of the applied stimulation signal to the exterior part, so that the stimulation signal is applied to the exterior part based on the exterior part data. The stimulation signal may be an electric signal applied to the exterior part by a stimulation device comprising e.g. an emission coil. The stimulation device is placed in the proximity of the exterior part and activated to emit a time-dependent electromagnetic signal onto the exterior part, where it induces a further time-dependent electric signal. That electric signal is transmitted from the exterior part into the nerve fibre so that the electric potential in the nerve fibre increases. Specifically, the exterior part has an electrically conducting connection to the nerve fibre, for example the nerve fibre is directly connected to the exterior part, for example runs into or through it. The nerve fibre will then in turn emit an emitted stimulation signal which will be time-dependent in a manner comparable or identical to the applied stimulation signal.

In a further (for example fifth) exemplary step, check signal data is acquired which describes an emitted stimulation signal emitted by the nerve fibre. The check signal data is in one example acquired based on the exterior part data. The check signal data has been generated based on an electric or electromagnetic signal generated by measuring the emitted stimulation signal with a measurement device such as an induction coil. The measurement device (also called detection device) is in one example included in an electrode insertable (for example, inserted) in the anatomical body part. In one example, the measurement device has been positioned relative to (for example, in the proximity of or at the position of) the nerve fibre for generation of the check signal data. The electrode may be a deep brain stimulation (DBS) electrode, for example a directional DBS electrode having a plurality of discrete and for example spaced-apart contacts for each emitting an electric stimulation field representing the applied stimulation signal at a predetermined voltage and frequency. In one example, the electrode is an MER electrode (micro-electrode recording). The electrode is inserted for example into the brain to a position which is assumed to be in the proximity of the nerve fibre. Insertion of the electrode into the anatomical body part is in one example not part of, for example not encompassed by the disclosed method. Rather, the disclosed method merely processes the data describing the emitted stimulation signal. For example, the emitted stimulation signal may be detected and stored in digital form before the disclosed method is executed. In this case, the method merely encompasses reading of the stimulation signal data which defines the signal properties such as at least one of voltage or frequency of the emitted stimulation signal.

Generally, it will be desired that application of the applied stimulation signal by the stimulation device stimulates a predetermined (at least one of known or desired) nerve fibre via the exterior part. Actually placing the induction coil is not necessarily part of the disclosed method, but may be a part of it. The disclosed method in any case encompasses reading the measurement data received from the measurement device which may be stored in an electronic data storage device and read by the disclosed method sometime after the measurement data was taken. The position at which the stimulation device needs to be positioned relative to the exterior part so as to stimulate the exterior part is determined for example using a navigation system. For example, a marker device is attached to the stimulation device in a predetermined (at least one of known or fixed) relative position. The marker device is suitable for optically navigating the position of the stimulation device by using a stereotactic navigation system which also knows the position of the exterior region in the reference system used for the optical navigation, for example from predetermined positional information included in the medical image data. Thus, the stimulation device can be navigated to a position relative to the exterior part which is suitable for stimulation of the exterior part by the stimulation device.

The emitted stimulation signal generally is a time-dependent electric signal such as an alternating current and/or an alternating electromagnetic field. If the measurement device (e.g. the induction coil) is placed in such an electromagnetic field, this will induce a measurement current in the induction coil which has physical properties (such as frequency) which allow comparing it to the corresponding known properties described by the stimulation signal data. This allows detecting whether the predetermined nerve fibre has been stimulated: if the measurement device is placed over an exterior part known to be connected to the predetermined nerve fibre, and if applying the applied stimulation signal leads to detection of a corresponding (comparable) emitted stimulation signal in the proximity of the nerve fibre, it will be justified to assume that the predetermined nerve fibre has been stimulated with the applied stimulation signal and that the electrode measuring the emitted stimulation signal was placed correctly relative to the position of the predetermined nerve fibre when applying the applied stimulation signal. It can then be further assumed that that position of the electrode is also suitable for using the electrode to stimulate the nerve fibre. If no emitted stimulation signal is detected, it will be justified to assume that the predetermined nerve fibre was not stimulated despite application of the applied stimulation signal by the stimulation device. This will be an indicator that the electrode for detecting the emitted stimulation signal was not placed correctly relative to the position of the predetermined nerve fibre when applying the applied stimulation signal. It can then be further assumed that that position of the electrode is not suitable for using the electrode to stimulate the nerve fibre. This procedure therefore allows finding a position of the electrode suitable for deep brain stimulation via the electrode.

In a further (for example sixth) exemplary step, correspondence measure data is determined which describes a measure of correspondence between the applied stimulation signal and the emitted stimulation signal. This includes specifically determining (e.g. measuring) a value of the correspondence measure. The correspondence measure data is determined based on the stimulation signal data and the check signal data. For example, the correspondence measure data is determined by comparing the applied stimulation signal to the emitted stimulation signal. The correspondence measure describes a degree of correspondence of the measured emitted stimulation signal to the applied stimulation signal. This degree of correspondence allows determining whether the emitted stimulation signal is sufficiently similar to justify the determination (assumption) that the predetermined nerve fibre was stimulated by application of the applied stimulation signal. To that end, the determined value of the correspondence measure is compared to a predetermined value of the correspondence measure which is taken is being sufficient to justify the determination (assumption) that the predetermined nerve fibre was stimulated by application of the applied stimulation signal.

In a further exemplary step of the disclosed method, reaction signal data describing a reaction signal of the anatomical body part in reaction to the applied stimulation signal is determined. The reaction signal is described by for example at least one of an impedance-related quantity (for example, impedance) or a comparison measure in the spectral domain of for example an electric signal induced in the contacts of the electrode by the reaction of the nerve fibre (e.g. an alternating current) in reaction to the applied stimulation signal, for example a cross-correlation-based measure (specifically, a cross-correlation). The correspondence measure data can then be determined based on also the reaction signal data.

In one more specific example, the impedance-related quantity is determined, and the method comprises:
 acquiring stimulation impedance data describing (for example defining or representing) an impedance of the anatomical body part while the applied stimulation signal is being applied;
 determining, based on the stimulation impedance data and the stimulation signal data, impedance change data describing (for example, defining or representing) a comparison of a time-dependent change of the impedance while the applied stimulation signal is being applied to the applied stimulation signal.

It is known that the impedance of the anatomical body part decreases when the applied stimulation signal is applied to the anatomical body part, specifically to the nerve fibre which is located in the anatomical body part. The impedance can be measured between contacts of the electrode when the electrode has been inserted into the anatomical body part, and the impedance depends on the type of tissue forming the anatomical body part. Typical (predetermined) impedance values of different tissue types are known. Comparison of the measured impedance to the predetermined tissue values therefore allows determining the tissue type of the anatomical body part. The sampling rate for the impedance measurement should have the same frequency as the applied stimulation signal, and the impedance measurement in one example occurs in a time-synchronized manner to application of the applied stimulation signal, i.e. the impedance measurement should start when the application of the applied stimulation signal starts and the impedance measurement should end when the application of the applied stimulation signal ends. In one example of the disclosed method, the frequency of the impedance decrease is determined from the measured impedance values. A peak of the frequency spectrum of the impedance decrease is expected to lie around the frequency of the applied stimulation signal.

This example of the disclosed method therefore encompasses in one variant determining the peak value of the frequency spectrum of the impedance decrease, and comparing that peak value to the (predetermined) frequency of the applied stimulation signal (which may typically lie at or around 15 Hz). If the comparison results in that the peak value lies at least within a predetermined interval around the frequency of the applied stimulation signal, it is determined that the applied stimulation signal was applied (as desired) to the surrounding tissue, i.e. to the anatomical body part. If the comparison results in that the peak value does not lie at least within a predetermined interval around the frequency of the applied stimulation signal, it is determined that the applied stimulation signal was not applied (as desired) to the tissue surrounding the measurement device.

In an alternative variant, the average impedance during application of the applied stimulation signal may be determined and compared to the average impedance while the applied stimulation signal is not being applied. A difference between the average values that fulfils a predetermined criterion (such as having a predetermined relationship relative to a threshold value, e.g. being less or greater or equal to the threshold value) is then used as an indicator that the emitted stimulation signal has been detected by the measurement device and that the measurement device (electrode) is thus positioned as desired relative to the nerve fibre, for example so as to be suitable for stimulation of the nerve fibre by the measurement device (electrode).

In another more specific example, the comparison measure in the spectral domain is determined, and the method comprises:
  acquiring stimulation signal spectrum data describing (for example, defining or representing) a power spectrum of an electric signal effected by the applied stimulation signal while the applied stimulation signal is being applied;
  determining, based on the stimulation signal spectrum data and the stimulation signal data, spectral comparison data describing (for example, defining or representing) a comparison of the power spectra.

When the applied stimulation signal is applied as desired to the exterior part, an electric stimulation of the tissue in the anatomical body part occurs via the nerve fibre. This electric stimulation may vary in at least one of strength and frequency according to the strength and frequency of the applied stimulation signal, and accordingly effect (specifically, induce) an electric signal in the electrode. The contacts of the electrode will therefore experience an electromagnetic excitation corresponding at least substantially at least in frequency to the applied stimulation signal. That excitation is the aforementioned electric signal and occurs (only) over the same time as the application of the applied stimulation signal. This example of the disclosed method therefore encompasses determining the peak value of the frequency spectrum of the occurrence of that electric signal, and comparing that peak value to the (predetermined) frequency of the applied stimulation signal (which may typically lie at or around 15 Hz). The peak value may also be determined by comparing the frequency spectrum of the applied stimulation signal to a frequency spectrum of a signal detected by the measurement device while the applied stimulation signal is (was) not being applied. If the comparison results in that the peak value lies at least within a predetermined interval around the frequency of the applied stimulation signal, it is determined that the applied stimulation signal was applied (as desired) to the tissue surrounding the measurement device, and was detected (as desired) by the measurement device (the electrode). It can then be determined that the electrode is placed correctly relative to the nerve fibre. If the comparison results in that the peak value does not lie at least within a predetermined interval around the frequency of the applied stimulation signal, it is determined that the applied stimulation signal was not applied (as desired) to the tissue surrounding the measurement device and that the measurement device (the electrode) was therefore not placed in proximity of the predetermined nerve fibre.

Determining the impedance-related quantity or the comparison measure in the spectral domain therefore allows for checking whether the applied stimulation signal was applied (as desired) to the anatomical body part, specifically to the tissue surrounding the electrode. This allows deducing information as to whether the electrode has a predetermined (desired) position relative to the (predetermined) nerve fibre.

In one example of the disclosed method, nerve fibre stimulation data is determined which describes (for example, defines or represents) whether the (predetermined) nerve fibre has been (or was) stimulated by the applied stimulation signal. The nerve fibre stimulation data is determined based on the correspondence measure data. If the correspondence measure is an impedance-related quantity, the nerve fibre stimulation data may be determined additionally based on the impedance comparison data. If the determined value of the correspondence measure has a predetermined relation to the predetermined value of the correspondence measure, a certain determination is made for placement of the electrode when applying the applied stimulation signal. For example, if the determined value is equal to or larger than the predetermined value, it is determined that the electrode was correctly placed for stimulating the predetermined nerve fibre. If, on the contrary, the determined value is lower than the predetermined value, it is determined that the electrode was not correctly placed for stimulating the predetermined nerve fibre.

In one example of the disclosed method, a device used for applying the applied stimulation signal (e.g. an electrode introduced into the anatomical body part e.g. in the proximity of the predetermined nerve fibre) and a device used for generating the emitted stimulation signal (a measurement device such as an electromagnetic measurement device including an induction coil) have been time-synchronized. In one more specific variant of this example, the applied stimulation signal and the emitted stimulation signal have an actual (e.g. measured) temporal relationship (such as a time shift) relative to one another. In a further example of the disclosed method, the atlas data comprises information corresponding to an expected temporal relationship between the applied stimulation signal and the emitted stimulation signal. That information is compared to the actual temporal relationship in order to deduce, based on the result of the comparison, physiological information such as whether the nerve fibre has demyelinised or not. In particular, the time required for the stimulation signal to travel through the nerve fibre can be determined that way, and that time depends on the degree of demyelinisation of the nerve fibre.

This method according to the first aspect is applicable for example to the case in which the position of the exterior part (which is to be stimulated) is determined in-vivo by using fibertractographic methods on the basis of patient-specific diffusion weighted magnetic resonance imaging data, utilizing the proposed target position of the deep brain stimulation electrode or the detected actual intraoperative position of the deep brain stimulation electrode as tractographic seed region.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

In a seventh aspect, the invention is directed to a (physical, for example electrical, for example technically generated) signal wave, for example a digital signal wave, carrying information which represents the program according to the second aspect.

In an eighth aspect, the invention is directed to a medical system for determining a stimulation of a nerve fibre disposed in an anatomical body part of a patient's body, the system comprising:
  a) the at least one computer according to fourth aspect;
  b) at least one electronic data storage device storing at least one of the medical image data or the atlas data or the stimulation signal data; and
  c) a measurement device (e.g. an electromagnetic measurement device such as one comprising an induction coil for measuring an induced electric signal) for measuring the emitted stimulation signal, the measurement device being operably coupled to the at least one computer for transmitting a signal to the at least one computer corresponding to the check signal data,
  wherein the at least one computer is operably coupled to the at least one electronic data storage device for acquiring, from the at least one data storage device, at least one of the medical image data or the atlas data or the stimulation signal data.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of therapy or surgery. More particularly, the invention does not involve or in particular comprise or encompass any surgical or therapeutic activity. The invention is instead directed as applicable to reading data corresponding to an electric signal applied to a nerve fibre (the applied stimulation signal) and emitted from an exterior part (the emitted stimulation signal) which has an electrically conducting connection to the nerve fibre. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a computer-based navigation system and can be a stereotactic camera which is sensitive to electromagnetic waves in a predetermined wavelength range such as the infrared wavelength range or any other wavelength range with which the marker are irradiated and which is reflected by the marker. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 is a flow diagram illustrating the basic steps of the disclosed method in accordance with the first aspect, which in the illustrative example of FIG. 1 starts with a step S1.1 of acquiring the patient image data. In subsequent step S1.2, the atlas data is acquired, followed by step S1.3 which encompasses determining the exterior part data. Then, step S1.4 acquires the stimulation signal data. Steps S1.1, S1.2, serve as input steps for step S1.3, and step S1.3 serves as an input step to step S1.4. Step S1.5 is directed to acquiring the check signal data. Finally, steps S1.1 to S1.5 serve as input steps for the last step of FIG. 1 which is step S1.6 encompassing determination of the correspondence measure data.

Figure 1:
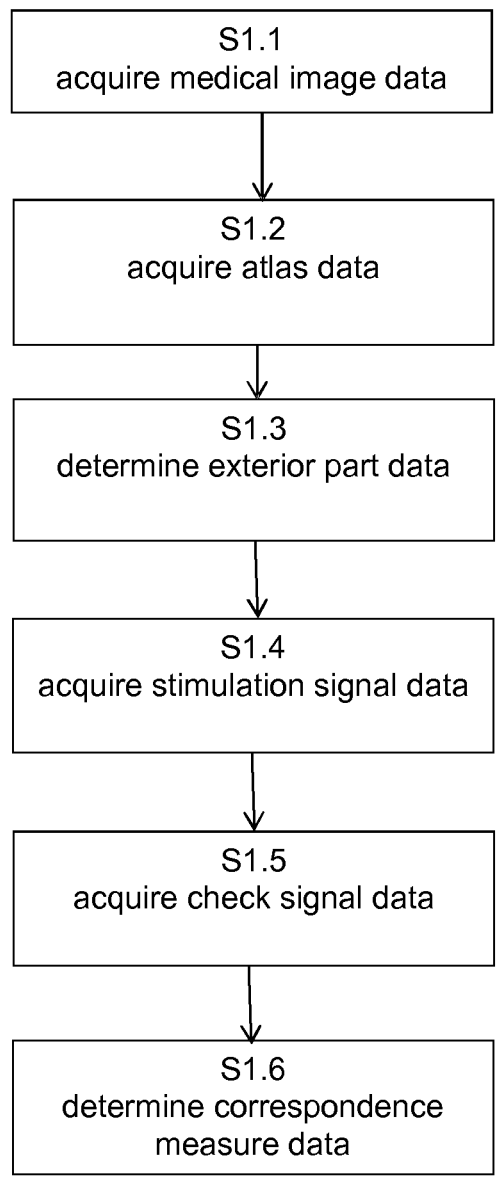
FIG. 1 is a flow diagram showing the basic steps of the disclosed method according to the first aspect.
Figure 2:
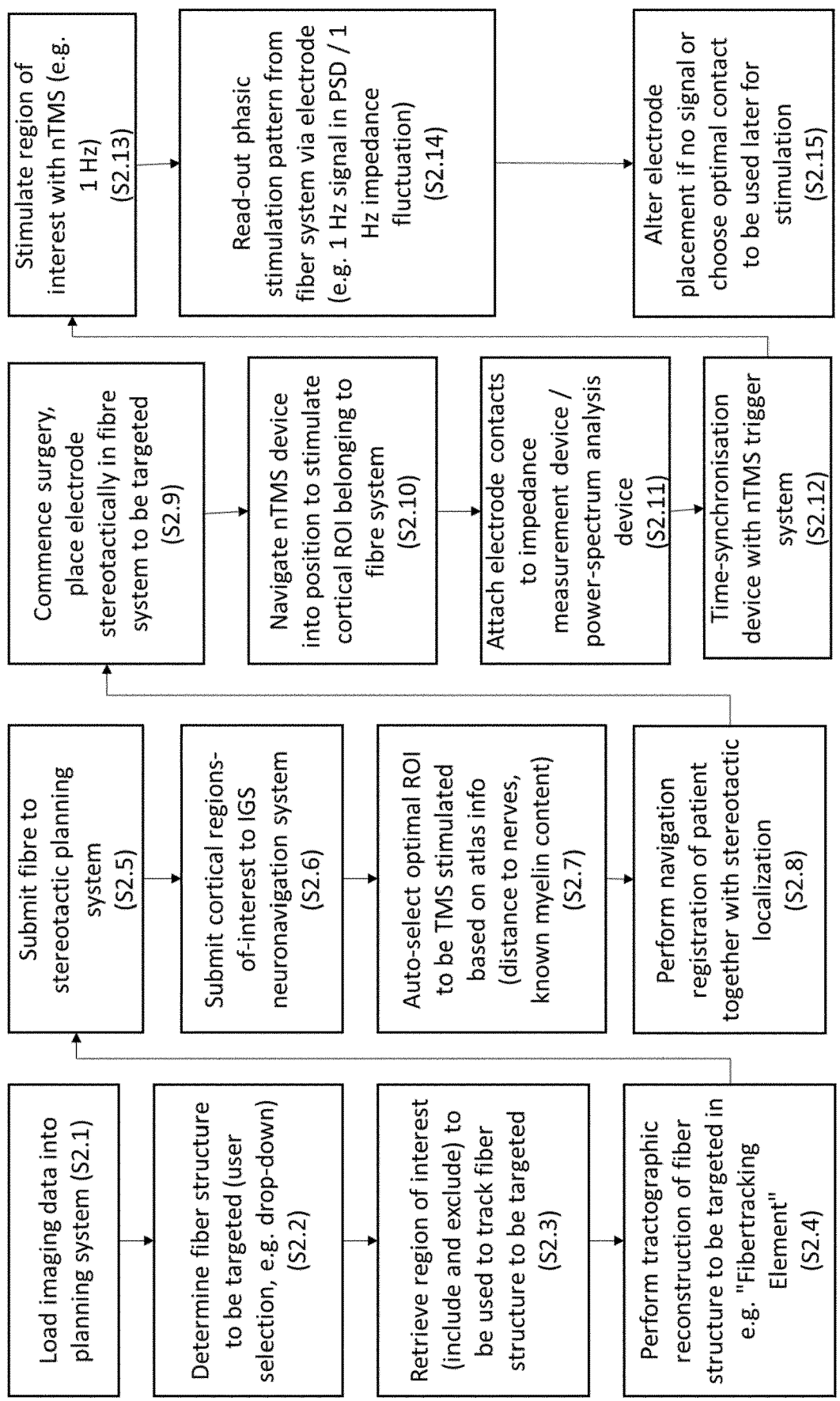
FIG. 2 is a flow diagram showing a detailed example of the disclosed method according to the first aspect.

According to FIG. 2, the imaging data (corresponding to the medical image data is in step S2.1 acquired by (loaded into) a computer of a planning system. From the digital image, the fibre structure, i.e. nerve fibre or bundle of nerve fibres) to be targeted by the stimulation is determined in step S2.2 e.g. by user selection using for example a drop-down menu. Then, in step S2.3, a region of interest (ROI) to be used to track the fibre structure to be targeted by including and/or including in step S2.3 certain parts of the anatomical body part such as the brain. Subsequently, tractographic fibre reconstruction is performed in step S2.4 using e.g. the "Fibertracking Element" software module provided by Brainlab AG. The algorithm then carries on with step S2.5 in which the tracked fibre is submitted to a stereotactic planning system, and with step S26. In which cortical regions of interest are submitted to an IGS neuronavigation system. This allows for auto-selection of an optimal ROI to be stimulated using TMS (Transcranial Magnetic Stimulation) in step S2.7 based on atlas information (the atlas data) based on for example their distance to nerve fibres or the known myelin content of the respective nerve fibres. Then, navigation registration of the patient together with stereotactic localization is performed in step S2.8, and surgery commences in step S2.9 to place the electrode stereotactically, i.e. using stereotactic navigation) in the fibre system to be targeted. Then, an nTMS (navigated Transcranial Magnetic Stimulation) device is navigated into position in step S2.10 to stimulate a cortical ROI belonging to the fibre system. Electrode contacts are attached to an impedance measurement device or power spectrum analysis device in step S2.11, and the respective measurement device is time-synchronized with an nTMS trigger system ins step S2.12. Then, the region of interest is stimulated with nTMS at a frequency of e.g. 1 Hz in step S2.13. The phasic stimulation pattern is read out from the fibre system via the DBS electrode which may be an MER electrode (micro-electrode recording). For example, a 1 Hz signal is determined in the power spectrum density function, or 1 Hz impedance fluctuation is determined in step S2.14.

If the measure of correspondence is an impedance-related quantity, the impedance measurements for each electrode contact during the phasic stimulation are compared with baseline measurements acquired prior and after the phasic stimulation phase. Contacts which are affected by the stimulation will display physically decreased impedance values, thereby identifying them as being positioned along or within stimulated pathways.

If the measure of correspondence is a comparison measure in the time spectral domain, local field potential data is acquired from the implanted electrodes during or after the surgical procedure, descriptive metrics (such as power for a given frequency-band) for time series data on channels connected to each electrode contact during the phasic stimulation are compared with baseline measurements acquired prior and after the phasic stimulation phase. Here the contacts which are affected by the stimulation will display statistically significant differences in power in the frequency-band containing the stimulation frequency (e.g. if stimulated with a 15 Hz TMS pulse the low-beta Band 2-20 Hz will be affected most strongly) during the stimulation time window, thereby identifying them as being positioned along or within stimulated pathways. For such a procedure, multiple stimulation periods are interleaved with non-stimulation periods of equal length, extraction of power values and subsequent t-test significance testing is utilized to identify the affected contacts. In an alternative method signal decomposition/dimensionality reduction methods (e.g. temporal Independent Component Analysis) can be applied to the time series data on various channels (recorded from single contacts), after decomposition certain components (e.g. Independent Components) will show a phasic change during the stimulation period on affected channels.

If it is determined in step S2.15 that in step S2.14 no signal was detected, the electrode placement can be altered. If the signal is detected as desired in step S2.14, an optimal contact of the electrode can be chosen in step S15 for later use during stimulation.

Figure 3:
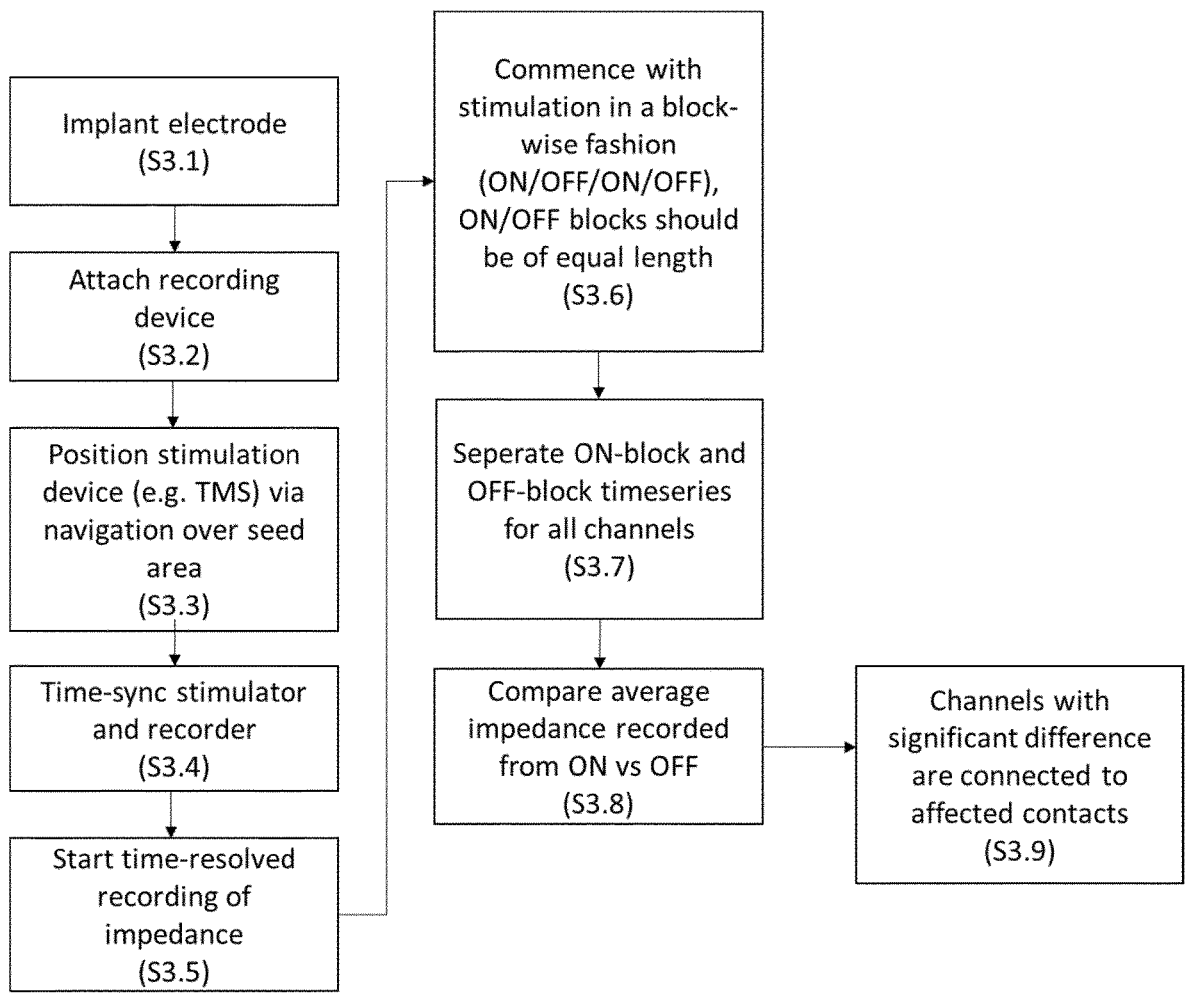
FIG. 3 is a flow diagram showing the example of the disclosed method according to the first aspect in which the correspondence measure is impedance.

FIG. 3 shows the example of determining the correspondence measure by impedance measurement. Again, the electrode is implanted in step S3.1, and a recording device is attached to it in step S3.2. The stimulation device is positioned via optical navigation over the seed area (i.e. the exterior part) in step S3.3. Then, the stimulator (stimulation device) and the recorder (measurement/detection device) are time-synchronized in step S3.4. The time-resolved recording of impedance values ensues in step S3.5, and step S3.6 commencers with the stimulation in a block-wise fashion (i.e. in intervals of the applied stimulation signal being ON or OFF, the sequence of intervals being e.g. periodically repeated. The blocks of ON and OFF should be of equal length in time. Separate ON- and OFF-block time series should be applied to all available channels in step S3.7. The average impedance recorded during blocks of ON (i.e. while the applied stimulation signal is being applied) is compared in step S3.8 to the average impedance recorded during block of OFF (i.e. while the applied stimulation signal is not being applied). In step S3.9 it is then determined that channels with a significant difference in the average impedance are connected to affected contacts which have recorded the emitted stimulation signal.

Figure 4:
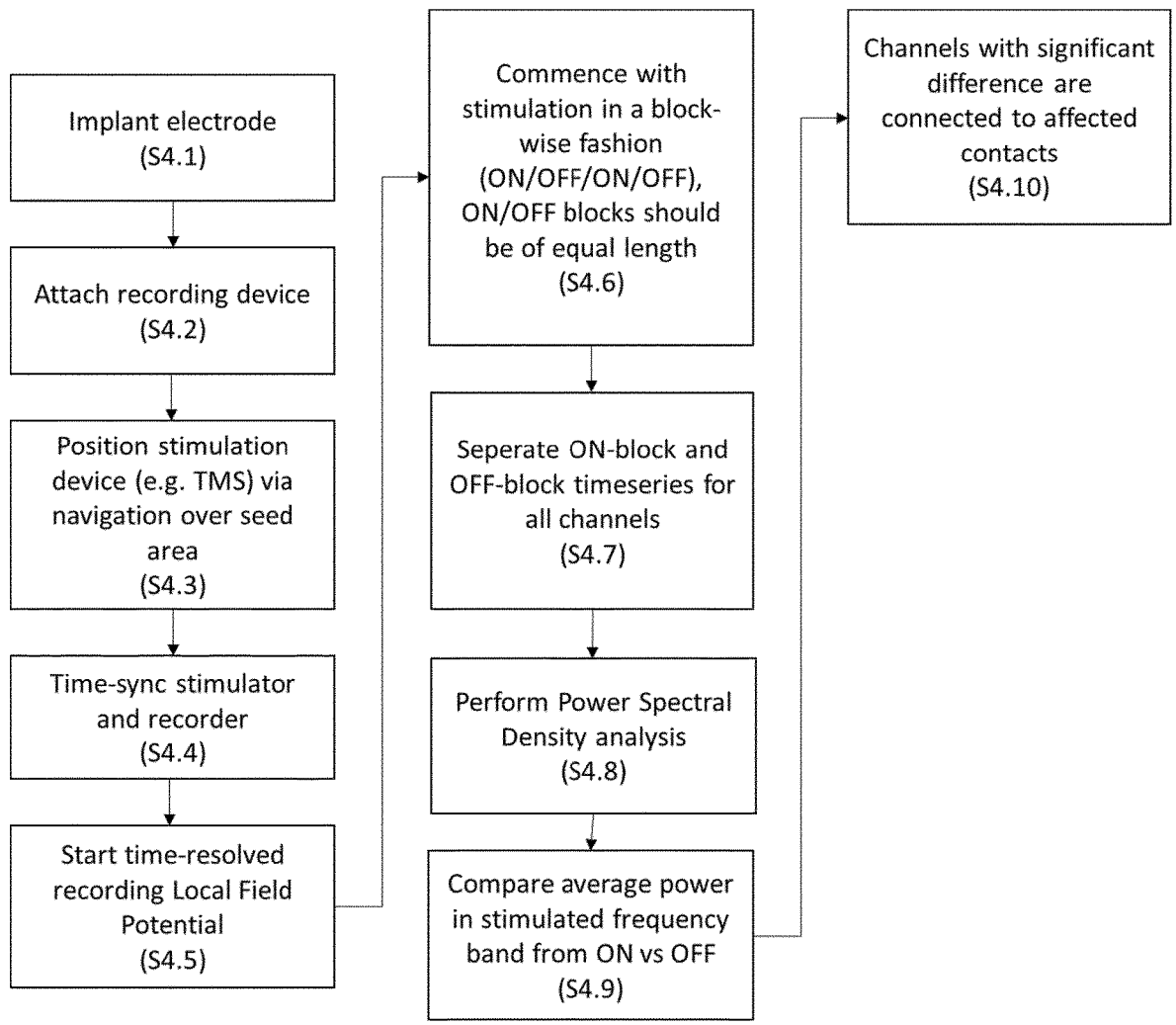
FIG. 4 is a flow diagram showing the example of the disclosed method according to the first aspect in which the correspondence measure is a spectral quantity.

FIG. 4 shows the example of determining the correspondence measure by spectral analysis. Again, the electrode is implanted in step S4.1, and a recording device is attached to it in step S4.2. The stimulation device is positioned via optical navigation over the seed area (i.e. the exterior part) in step S4.3. Then, the stimulator (stimulation device) and the recorder (measurement/detection device) are time-synchronized in step S4.4. Then, time-resolved recording of the local (electric) field potential around the measurement device (electrode) is started in step S4.5. Step S4.6 commencers with the stimulation in a block-wise fashion (i.e. in intervals of the applied stimulation signal being ON or OFF, the sequence of intervals being e.g. periodically repeated. The blocks of ON and OFF should be of equal length in time. Separate ON- and OFF-block time series should be applied to all available channels in step S4.7. A power spectral density analysis is performed in step S4.8, and the average power in the stimulation frequency band for the ON-intervals is compared in step S4.9 to the average power for the OFF-intervals. In step S4.10 it is then determined that channels with a significant difference in the average power are connected to affected contacts which have recorded the emitted stimulation signal.

Figure 5:
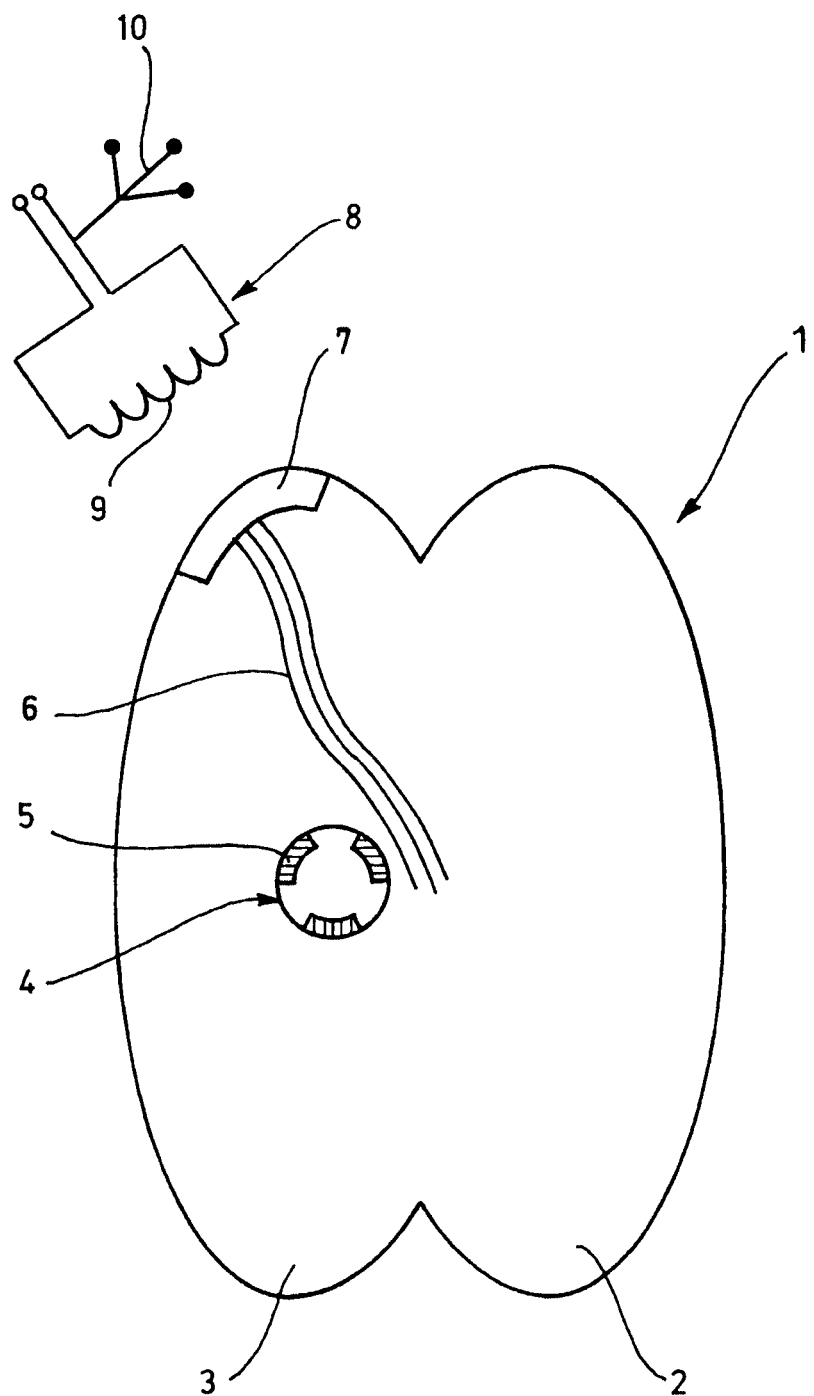
FIG. 5 illustrates use of the system according to the eighth aspect.

FIG. 5 shows a setup usable for implementing the method according to the first aspect which is also part of the system according to the eighth aspect. Illustrated is an anatomical body part 1 represented by a brain having two brain halves 2, 3. A measurement device embodied by a directional electrode 4 having a plurality of contacts 5 is placed in the proximity of a bundle of nerve fibres 6 which are connected to an exterior part embodied by a cortex region 7. A stimulation device 8 including an emission coil 9 for emitting (applying) the applied stimulation signal is placed in a suitable position relative to the cortex region 7. The stimulation device 8 is provided with a marker array (reference star) 10 having retroreflective spherical markers which are optically trackable using a stereotactic camera so as to determine their position in a positional reference system used by a navigation system (not shown).

The disclosed method and system provide for the following features, functionalities and advantages:

- A patient has been implanted with a brain stimulation device such as a DBS electrode or a cortical stimulation grid.
- Beyond active stimulation capabilities the implanted device has at least one sensing function, either simple impedance measurement at the contacts or direct electrical recording of frequencies.
- The patients anatomical data has been processed using Universal Atlas Segmentation, the implant localized in post-operative imaging (e.g. CT) and the surrounding fiber connections been tractographically reconstructed using fiber tracking.
- Using a navigation (IGS—image-guided surgery) system, a brain stimulator is brought into position (e.g. nTMS) and the brain is stimulated in that zone
- When the fibers in the vicinity of the to be tuned (e.g. directional DBS) stimulator are activated the impedance drops
- This way the stimulation direction of the system can be tuned towards the provoked impedance change thereby optimally stimulating the fibers connecting the stimulator to the e.g. nTMS stimulated region
- The same principal can be applied with cortical stimulation or with sensing instead of impedance measurements, by provoking predictable changes in the power spectral composition through electrical stimulation the system can be tuned as well in a non-impedance based workflow.

For example, in depression, the fronto-polar Brodman Area 10 is known to be involved in certain functions related to mood and fibers originating from BA10 are traversing through the medial forebrain bundle, however implantation and correct directed stimulation of the MFB remains challenging. nTMS stimulation of BA10 originating fibers could allow to tune stimulation to encompass the right fibers Through optimizing brain stimulation to optimally cover the desired to-be-stimulated fibers patient outcome can be optimized in a manner that does not necessarily involve invasive procedures or behavior provocation paradigms.

A specific feature of the disclosed method is the timed connection of stimulation, sensing/impedance measurement and in turn the automated orientation of stimulation through a GUIDE-like algorithm.

In one example, BOLD or PET imaging data are used to determine the stimulation regions that shall provoke changes at the site of the stimulator to be tuned.

In one example, stimulation strengths are kept so low that no perceptible effect is subjectively experienced by the subject, thereby greatly increasing patient comfort for these test scenarios.

In one example, simultaneous bilateral implantation of stimulators is complemented by stimulating fibers with one system and tuning the other and vice versa.

In one example, the excitability information (of the cortex) is used directly to inform optimal DBS stimulation levels.

In one example, this is used to determine the actual orientation of D-lead electrode in the brain.

The invention claimed is:

1. A computer-implemented method for determining a stimulated nerve fibre disposed in an anatomical body part of a patient's body, the method comprising executing, on at least one processor of at least one computer, steps of:
   acquiring, at the at least one processor, medical image data describing a digital image of the anatomical body part, wherein the anatomical body part contains at least one nerve fibre extending in a direction between an internal part of the anatomical body part and an exterior part of the anatomical body part;
   acquiring, at the at least one processor, atlas data describing an image-based model of the anatomical body part including a representation of the at least one nerve fibre;
   determining, by the at least one processor, exterior part data describing a position of the exterior part in the anatomical body part and an association between the exterior part and the at least one nerve fibre by transforming and fusing the medical image data and the atlas data;
      wherein the medical image data, represented by at least one of a pixel or a voxel, is mapped to the atlas data in a positional reference system, to generate the exterior part data;
   acquiring, at the at least one processor, stimulation signal data describing a predetermined stimulation signal that is applied to the exterior part by a stimulation device, wherein the stimulation device is positioned over the exterior part based on the exterior part data describing the position of the exterior part in the anatomical body part and indicating the at least one nerve fibre runs into or through the exterior part, wherein the stimulation signal data describes one or more known physical properties;
   acquiring, at the at least one processor, check signal data describing an emitted stimulation signal emitted by the at least one nerve fibre in response to application of the predetermined stimulation signal, wherein the emitted stimulation is measured using a directional electrode positioned in the anatomical body part relative to the at least one nerve fibre, and wherein the check signal data further describes the result of a measurement of one or more physical properties;
   determining, by the at least one processor and based on the stimulation signal data and the check signal data, correspondence measure data describing a degree of correspondence between the predetermined stimulation signal and the emitted stimulation signal, to determine whether the emitted stimulation signal is similar to the predetermined stimulation signal,
      wherein determining the correspondence measure data includes comparing the one or more known physical properties described by the stimulation signal data to one or more physical properties described by the check signal data;
   determining, by the at least one processor, whether the at least one nerve fibre was stimulated by application of the predetermined stimulation signal based on the degree of correspondence; and
   determining, by the at least one processor, whether a rotational orientation of the directional electrode that is positioned in the anatomical body part is correctly placed relative to the at least one nerve fibre based on the correspondence measure data.

2. The method according to claim 1, comprising:
   determining, by the at least one processor, nerve fibre stimulation data describing whether the at least one nerve fibre has been stimulated by the predetermined stimulation signal based on the correspondence measure data.

3. The method according to claim 1, wherein the association between the exterior part and the at least one nerve fibre comprises at least one of a relative position between the exterior part and the at least one nerve fibre or a nerve stimulus-propagating connection between the exterior part and the at least one nerve fibre.

4. The method according to claim 1, wherein the check signal data has been generated based on an electric or electromagnetic signal generated by measuring the emitted stimulation signal with a measurement device.

5. The method according to claim 1, wherein the correspondence measure data is determined by comparing the predetermined stimulation signal to the emitted stimulation signal.

6. The method according to claim 1, wherein reaction signal data describing a reaction signal of the anatomical body part in reaction to the predetermined stimulation signal is determined, and wherein the correspondence measure data is determined further based on the reaction signal data.

7. The method according to claim 6, wherein the reaction signal is described by an impedance-related quantity, and wherein the method comprises:
   acquiring, at the at least one processor, stimulation impedance data describing an impedance of the anatomical body part while the predetermined stimulation signal is being applied;
   determining, by the at least one processor, impedance change data describing a comparison of a time-dependent change of the impedance while the predetermined stimulation signal is being applied to the anatomical body part based on the stimulation impedance data and the stimulation signal data.

8. The method according to claim 7, wherein the nerve fibre stimulation data is determined based on the impedance comparison data.

9. The method according claim 6, wherein the reaction signal is described by a comparison measure in a spectral domain, and wherein the method comprises:
   acquiring, at the at least one processor, stimulation signal spectrum data describing a power spectrum of an electric signal effected by the predetermined stimulation signal while the predetermined stimulation signal is being applied;
   determining, by the at least one processor, spectral comparison data describing a comparison of the power spectrum based on the stimulation signal spectrum data and the stimulation signal data.

10. The method according to claim 1, wherein a device used for applying the predetermined stimulation signal and a device used for generating the emitted stimulation signal have been time-synchronized.

11. The method according to claim 1, wherein the predetermined stimulation signal and the emitted stimulation signal have a time shift relative to one another.

12. The method according to claim 11, wherein the atlas data comprises information corresponding to art expected temporal relationship between the predetermined stimulation signal and the emitted stimulation signal, and wherein that information is compared to the predetermined temporal relationship in order to deduce, by the at least one processor, physiological information based on the result of the comparison.

13. The method according to claim 1, wherein the medical image data has been generated by applying a diffusion-weighted magnetic resonance imaging modality to the anatomical body part.

14. The method according to claim 1, wherein the measurement of the one or more physical properties includes impedance values measured between contacts of the directional electrode that is implanted in the anatomical body part relative to the at least one nerve fibre and that generates the check signal data.

15. The method according to claim 14, wherein a frequency of impedance decrease is determined from the measured impedance values.

16. The method according to claim 14, wherein comparing the one or more known physical properties described by the stimulation signal data to the one or more physical properties described by the check signal data comprises:
   comparing a peak value of a frequency spectrum of an impedance decrease to a frequency of the applied predetermined stimulation signal, to determine whether the peak value lies at least within a predetermined interval around the frequency of the applied predetermined stimulation signal.

17. A non-transitory computer-readable storage medium comprising instructions, which when running on at least one processor, causes the at least one processor to perform the steps of:
   acquiring, at the at least one processor, medical image data describing a digital image of an anatomical body part, wherein the anatomical body part contains at least one nerve fibre extending in a direction between an internal part of the anatomical body part and an exterior part of the anatomical body part;
   acquiring, at the at least one processor, atlas data describing an image-based model of the anatomical body part including a representation of the at least one nerve fibre;
   determining, by the at least one processor, exterior part data describing a position of the exterior part in the anatomical body part and an association between the exterior part and the at least one nerve fibre by transforming and fusing the medical image data and the atlas data;
      wherein the medical image data, represented by at least one of a pixel or a voxel, is mapped to the atlas data in a positional reference system, to generate the exterior part data;
   acquiring, at the at least one processor, stimulation signal data describing a predetermined stimulation signal that is applied to the exterior part by a stimulation device, wherein the stimulation device is positioned over the exterior part based on the exterior part data describing the position of the exterior part in the anatomical body part and indicating the at least one nerve fibre runs into or through the exterior part, wherein the stimulation signal data describes one or more known physical properties;
   acquiring, at the at least one processor, check signal data describing an emitted stimulation signal emitted by the at least one nerve fibre in response to application of the predetermined stimulation signal, wherein the emitted stimulation is measured using a directional electrode positioned in the anatomical body part relative to the at least one nerve fibre, and wherein the check signal data further describes the result of a measurement of one or more physical properties;

determining, by the at least one processor and based on the stimulation signal data and the check signal data, correspondence measure data describing a degree of correspondence between the predetermined stimulation signal and the emitted stimulation signal, to determine whether the emitted stimulation signal is similar to the predetermined stimulation signal, wherein determining the correspondence measure data includes comparing the one or more known physical properties described by the stimulation signal data to one or more physical properties described by the check signal data;

determining, by the at least one processor, whether the at least one nerve fibre was stimulated by application of the predetermined stimulation signal based on the degree of correspondence; and determining, by the at least one processor, whether a rotational orientation of the directional electrode that is positioned in the anatomical body part is correctly placed relative to the at least one nerve fibre based on the correspondence measure data.

18. A medical system for determining a stimulation of a nerve fibre disposed in an anatomical body part of a patient's body, the system comprising:

at least one computer having at least one processor and associated memory, the memory storing instructions which, when executed on the at least one processor, causes the at least one processor to:

acquire, at the at least one processor, medical image data describing a digital image of the anatomical body part, wherein the anatomical body part contains at least one nerve fibre extending in a direction between an internal part of the anatomical body part and an exterior part of the anatomical body part;

acquire, at the at least one processor, atlas data describing an image-based model of the anatomical body part including a representation of the at least one nerve fibre;

determine, by the at least one processor, exterior part data describing a position of the exterior part in the anatomical body part and an association between the exterior part and the nerve fibre by transforming and fusing the medical image data and the atlas data;

wherein the medical image data, represented by at least one of a pixel or a voxel, is mapped to the atlas data in a positional reference system, to generate the exterior part data;

acquire at the at least one processor, stimulation signal data describing a predetermined stimulation signal that is applied to the exterior part by a stimulation device, wherein the stimulation device is positioned over the exterior part based on the exterior part data describing the position of the exterior part in the anatomical body part and indicating the at least one nerve fibre runs into or through the exterior part, wherein the stimulation signal data describes one or more known physical properties;

acquire, at the at least one processor, check signal data describing an emitted stimulation signal emitted by the nerve fibre in response to application of the predetermined stimulation signal, wherein the emitted stimulation is measured using a directional electrode positioned in the anatomical body part relative to the at least one nerve fibre, and wherein the check signal data further describes the result of a measurement of one or more physical properties;

determine, by the at least one processor and based on the stimulation signal data and the check signal data, correspondence measure data describing a degree of correspondence between the predetermined stimulation signal and the emitted stimulation signal, to determine whether the emitted stimulation signal is similar to the predetermined stimulation signal, wherein the determination of the correspondence measure data includes a comparison of the one or more known physical properties described by the stimulation signal data to one or more physical properties described by the check signal data;

determine, by the at least one processor, whether the at least one nerve fibre was stimulated by application of the predetermined stimulation signal based on the degree of correspondence;

determine, by the at least one processor, whether a rotational orientation of the directional electrode that is positioned in the anatomical body part is correctly placed relative to the at least one nerve fibre based on the correspondence measure data;

at least one electronic data storage device storing at least one of the medical image data or the atlas data or the predetermined stimulation signal data; and a measurement device for measuring the emitted stimulation signal, the measurement device being included in the directional electrode and operably coupled to the at least one computer for transmitting a signal to the at least one computer corresponding to the check signal data, wherein the at least one computer is operably coupled to the at least one electronic data storage device for acquiring, from the at least one electronic data storage device, at least one of the medical image data or the atlas data or the predetermined stimulation signal data.

19. The medical system according to claim 18, wherein the atlas data contains positional information describing a relative position between the exterior part and the at least one nerve fibre in the image-based model.

20. The medical system according to claim 18, wherein the anatomical body part is a brain and the exterior part is a cortex.

* * * * *

UNITED STATES PATENT AND TRADEMARK OFFICE
CERTIFICATE OF CORRECTION

PATENT NO. : 12,011,290 B2
APPLICATION NO. : 16/336001
DATED : June 18, 2024
INVENTOR(S) : Bálint Varkuti It is certified that error appears in the above-identified patent and that said Letters Patent is hereby corrected as shown below:

In the Specification

In Column 1, Line 52, after 'activated' insert -- . --.

In Column 6, Line 1, delete "that that"" and insert -- that --, therefor.

In Column 6, Line 10, delete "that that"" and insert -- that --, therefor.

In Column 17, Line 34, delete "ins" and insert -- in --, therefor.

In Column 19, Line 44, after 'fibers' insert -- . --.

In the Claims

In Column 21, Claim 12, Line 64, delete "art" and insert -- an --, therefor.

Signed and Sealed this
Thirteenth Day of August, 2024

Katherine Kelly Vidal
*Director of the United States Patent and Trademark Office*